United States Patent [19]
Lai

[11] Patent Number: 5,512,205
[45] Date of Patent: * Apr. 30, 1996

[54] UV CURABLE CROSSLINKING AGENTS USEFUL IN COPOLYMERIZATION

[75] Inventor: Yu-Chin Lai, Pittsford, N.Y.

[73] Assignee: Bausch & Lomb Incorporated, Rochester, N.Y.

[*] Notice: The portion of the term of this patent subsequent to May 10, 2011, has been disclaimed.

[21] Appl. No.: 242,652

[22] Filed: May 9, 1994

Related U.S. Application Data

[63] Continuation of Ser. No. 922,452, Jul. 30, 1992, Pat. No. 5,310,779, which is a continuation-in-part of Ser. No. 884,481, May 15, 1992, abandoned, which is a continuation of Ser. No. 788,071, Nov. 5, 1991, abandoned.

[51] Int. Cl.$^6$ .................................................. C09K 3/00
[52] U.S. Cl. .......................... 252/182.14; 252/182.15; 252/182.17; 252/182.18; 252/182.23; 252/182.28
[58] Field of Search .................... 252/182.14, 182.15, 252/182.17, 182.18, 182.23, 182.28

[56] References Cited

U.S. PATENT DOCUMENTS

| | | | |
|---|---|---|---|
| 3,220,960 | 11/1965 | Wichterle | 260/2.5 |
| 3,330,664 | 7/1967 | Minsk et al. | 96/111 |
| 3,408,429 | 10/1968 | Wichterle | 264/1 |
| 3,496,254 | 2/1970 | Wichterle | 264/1 |
| 3,563,935 | 2/1971 | Beckmann et al. | 260/31.8 |
| 3,566,874 | 3/1971 | Shepherd et al. | 128/349 |
| 3,607,848 | 9/1971 | Stoy et al. | 260/86.1 |
| 4,084,459 | 4/1978 | Clark | 81/1 |
| 4,136,250 | 1/1979 | Mueller et al. | 528/29 |
| 4,153,641 | 5/1979 | Deichert et al. | 260/827 |
| 4,192,827 | 3/1980 | Mueller et al. | 525/123 |
| 4,197,266 | 4/1980 | Clark et al. | 264/1 |
| 4,486,577 | 12/1984 | Mueller et al. | 525/474 |
| 4,605,712 | 8/1986 | Mueller et al. | 525/474 |
| 4,740,533 | 4/1988 | Su et al. | 523/106 |
| 4,954,587 | 9/1990 | Mueller | 526/245 |
| 5,034,461 | 7/1991 | Lai et al. | 525/100 |
| 5,070,215 | 12/1991 | Bambury et al. | 556/418 |
| 5,310,779 | 5/1994 | Lai | 524/588 |

*Primary Examiner*—Edward J. Cain
*Attorney, Agent, or Firm*—Edward W. Black; Thomas John E.

[57] ABSTRACT

A novel class of compounds are disclosed which may be used as novel crosslinking agents for acrylic-containing, vinyl-containing and/or styrene-containing hydrophilic monomers to prepare novel UV-curable hydrophilic copolymers suitable for use as biomedical articles, especially contact lenses.

14 Claims, 1 Drawing Sheet

UV CURABLE CROSSLINKING AGENTS USEFUL IN COPOLYMERIZATION

This application is a continuation application of application Ser. No. 07/922,452 filed Jul. 30, 1992 now U.S. Pat. No. 5,310,779 which is a continuation-in-part application of Ser. No. 07/884,481 filed May 15, 1992, now abandoned, which is a continuation application of Ser. No. 07/788,071, filed Nov. 5, 1991 which is now abandoned.

BACKGROUND OF THE INVENTION

1. Field of the Invention

This invention relates to a novel class of compounds which may be used as novel crosslinking agents to prepare novel UV-curable hydrophilic copolymers suitable for use as articles in the biomedical field, especially contact lenses.

2. Background

In the field of crosslinked polymeric systems, initiators, and crosslinking compounds and compositions (crosslinkers) are often added to monomer mixes before polymerization. These crosslinkers facilitate formation of the desired polymer. In addition, crosslinkers can affect specific characteristics and mechanical properties of the resultant polymers.

Crosslinkers which are similar in structure to the monomers being reacted are often added to monomer mixtures. For example, a di(meth)acrylate or di(meth)acrylamide monomer would commonly be used as a crosslinker for a (meth)acrylate/(meth)acrylamide system. Alternatively, to react a vinyl-type system comprising N-vinyl pyrrolidone or vinyl acetate, for example, a vinyl-type crosslinker such as allyl methacrylate would ordinarily be used. For the purposes of this application, the terms, "vinyl-type" or "vinyl-containing" refer to those non-acrylic monomers having the vinyl grouping ($CH_2=CH-$), and which are generally reactive. "Acrylic-type" or "acrylic-containing" monomers refer to those monomers containing the acrylic grouping ($CH_2=CRCOX-$).

When a specific copolymeric system is desired which includes both a methacrylate-containing monomer and a non-acrylic vinyl-containing monomer, polymerization problems occur as a result of the varying reactivity of the two monomer types. In other words, non-acrylic vinyl-containing monomers are generally not reactive with the (meth)acrylate-containing monomers.

Therefore, to copolymerize N-vinyl pyrrolidone (NVP) with, for example, methyl methacrylate (MMA), allyl methacrylate has been used as a crosslinker with t-butylperoxy-octoate added as a thermal reaction initiator, and benzoin methyl ether (BME) as a photoinitiator. Such a monomer mix may then be first subjected to UV irradiation to polymerize the methacrylate groups, followed by heat curing to polymerize the allyl- and vinyl-containing monomers. This polymerization scheme is relatively cumbersome and may lead to polymeric systems having poor yields or a resulting polymer of poor optical quality. In addition, such resulting polymers may not be true crosslinked copolymers but may be mere nonhomogeneous interpenetrating polymer networks.

Alternately, a crosslinker such as allyl methacrylate could be used to assist the polymerization of the NVP/methacrylate system; however, this would also require heat curing. Heat curing is not as desirable as UV curing since overheating may adversely affect the desired properties of the end-product hydrogel. In addition, insufficient heat curing can result in a hydrogel which also fails to possess the desired end-result properties.

Other known crosslinking agents often used in polymeric syntheses are polyvinyl, typically di- or tri-vinyl monomers, most commonly the di- or tri(meth)acrylates of dihydric ethylene glycol, triethylene glycol, butylene glycol, hexane-1,6-diol, thio-diethylene glycol-diacrylate and methacrylate; neopentyl glycol diacrylate; trimethylolpropane triacrylate and the like; N,N'-dihydroxyethylene-bisacrylamide and -bismethacrylamides; also diallyl compounds like diallyl phthalate and triallyl cyanurate; divinylbenzene; ethylene glycol divinyl ether; and the (meth)acrylate esters of polyols such as triethanolamine, glycerol, pentanerythritol, butylene glycol, mannitol, and sorbitol. Further, illustrations include N,N-methylene-bis-(meth)acrylamide, sulfonated divinylbenzene, and divinylsulfone. Also useful are the reaction products of hydroxyalkyl (meth)acrylates with unsaturated isocyanates, for example the reaction product of 2-hydroxyethyl methacrylate with 2-isocyanatoethyl methacrylate (IEM) as disclosed in U.S. Pat. No. 4,954,587.

Other known crosslinking agents are the polyether-bisurethane-dimethacrylates as described in U.S. Pat. No. 4,192,827, and those crosslinkers obtained by reaction of polyethylene glycol, polypropylene glycol and polytetramethylene glycol with 2-isocyanatoethyl methacrylate (IEM) or m-isopropenyl-γ,γ-dimethylbenzyl isocyanates (m-TMI), and polysiloxane-bisurethane-dimethacrylates as described in U.S. Pat. Nos. 4,486,577 and 4,605,712. Still other known crosslinking agents are the reaction products of polyvinyl alcohol, ethoxylated polyvinyl alcohol or of polyvinyl alcohol-co-ethylene with 0.1 to 10 mol % vinyl isocyanates like IEM or m-TMI. However, none of the above-mentioned crosslinkers can be used to copolymerize vinyl and acrylic comonomers using only UV curing.

It is also known that NVP copolymerizes well with vinyl carbonates and vinyl carbamates. Specifically, NVP was shown to copolymerize with vinylene carbonate. The closeness of the reactivity ratios resulted in favorable random copolymerization. (See K. Hayashi and G. Smets, J. Polymer Science, Vol. 27, p. 275, (1958)). Further, it has been recently demonstrated that NVP can copolymerize with vinyl carbamates and carbonates with a UV sensitive initiator. (See U.S. Pat. No. 5,070,215).

It was discovered in the field that certain crosslinked polymeric materials could be hydrated and retain their water content. It was further found that the higher the water content within contact lenses made from these crosslinked hydrogel polymers, the greater was the oxygen permeability through the lens to the cornea.

In the field of contact lenses, various factors combine to yield a material that has appropriate characteristics. Oxygen permeability, wettability, material strength and stability are but a few of the factors which must be carefully balanced to achieve a useable end-result contact lens. Generally, as the water content of a hydrogel increases, oxygen permeability also increases. Since the cornea receives its oxygen supply exclusively from contact with the atmosphere, good oxygen permeability is a critical characteristic for any contact lens material.

In the case of hydrogel preparation, the crosslinkers affect specific mechanical properties relating to the firmness of the hydrogel, such as modulus, and tear strength. As a result, it is desirable in the field of hydrogel synthesis to introduce specific crosslinkers to copolymerize in a predictable way with the comonomers in the monomer mix, thereby creating hydrogels having certain desired properties.

A hydrogel is a hydrated crosslinked polymeric system that contains water in an equilibrium state. The physical properties of hydrogels can vary widely and are mostly determined by their water content. Hydrogels may contain 10% to 90% water by weight and exhibit excellent biocompatibilty. As a result there has been extensive interest in the use of hydrogels for various biomedical applications as biomedical devices. For example, hydrogels can be used as contact lenses, intraocular implants, membranes and other films, diaphragms, catheters, mouth guards, denture liners, tissue replacements, heart valves, intrauterine devices, ureter prostheses, etc. Commercial success for hydrogels has been found in the field of ophthamology, most particularly as contact lenses.

The use of hydrogels to make contact lenses has been known, since at least as early as Wichterle, et al., U.S. Pat. No. 3,220,960 which discloses hydrogels involving a hydrated polymer of an hydroxyalkyl acrylate or methacrylate crosslinked with a corresponding diester. Particularly, poly(2-hydroxyethyl methacrylate), also known as poly-HEMA, was disclosed as an illustrative hydrogel having a water content of about 39% by weight. Hydrogels such as 2-hydroxyethyl methacrylate with water contents of about 40% by weight, are often referred to as low water content hydrogels.

Another known hydrogel system is comprised of copolymers of N-vinyl pyrrolidone (NVP) and a methacrylate, such as methyl methacrylate (MMA). The water content of the NVP-MMA hydrogel systems can vary widely as a function of the ratio of NVP to MMA. However, most hydrogels derived from NVP and MMA which are of commercial interest have a water content in the 70% to 80% by weight range. Hydrogels containing N,N-dimethylacrylamide copolymers (DMA) are known to have similar properties. Hydrogels containing water weight percents in this range are often referred to as high water content hydrogels.

High water-containing hydrogels have at times exhibited undesirable mechanical properties. For example, such hydrogels are not easily formed into hydrolytically stable lenses. Further such materials have at times exhibited tearing or other breakage as a result of poor tensile strength. What was needed was a highly oxygen permeable material that was durable and highly wettable. Wettability is important in that if the lens is not sufficiently wettable, it does not remain lubricated and therefore cannot be worn comfortably on the eye. The optimal contact lens would have not only excellent oxygen permeability, but also excellent tear fluid wettability.

As a general rule, low Water content hydrogels have acceptable properties for application as soft contact lenses. High water content hydrogels appear to have acceptable oxygen permeability suitable for use as extended wear lenses. Extended wear lenses are those worn without removal for periods of time longer than a day. However, high water content hydrogels are often not easily formed into stable lenses. Such high water-containing lenses have been reported to tear more easily, and may otherwise be more prone to damage.

Theoretically, the most desirable lens would have oxygen transmissibility at least as high as that of lenses comprising the NVP-MMA system, while also having strength and mechanical properties similar to lenses made from the poly-HEMA hydrogels.

Silicone-containing materials were tried as viable contact lens materials and displayed very good oxygen permeability and durability. However, most silicone-containing materials are largely hydrophobic and therefore not sufficiently wettable. Further, it is believed that such hydrophobicity causes deposit problems, which may result in discomfort when wearing contact lenses made from these silicone-containing polymers. The optimum contact lens would have not only excellent oxygen permeability, but also excellent tear-fluid wettability.

As mentioned previously, curing hydrogels solely with UV radiation would be preferable to heat curing. However, no completely UV curable acrylic/vinyl- or styrene/vinyl- or acrylic/vinyl/styrene-crosslinked polymeric system, is presently known. Such a UV-curable polymeric hydrogel system employing a crosslinker able to compatibilize groups of varying reactivities would be highly advantageous.

SUMMARY OF THE INVENTION

In accordance with this invention novel crosslinking agents for UV-curable polymeric hydrogel systems are disclosed which comprise at least one vinyl-containing monomer and at least one of either a styrene-containing or an acrylic-containing monomer. The novel crosslinkers are able to polymerize hydrogel systems which contain in the monomer mix, both, at least one vinyl, and at least one of either a styrene or an acrylic group. The resulting, entirely UV-curable hydrogels derived from the monomeric mix therefore comprise at least one vinyl-containing monomer, at least one acrylic- or styrene-containing monomer, and a crosslinking agent derived from a novel class of crosslinkers. Alternatively, the monomeric mix may comprise at least one vinyl-, at least one acrylic- and at least one styrene-containing monomer and the novel crosslinker.

These novel crosslinkers have the schematic representation (I):

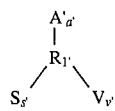
            I.

wherein

V denotes a vinyl-containing group having the formula:

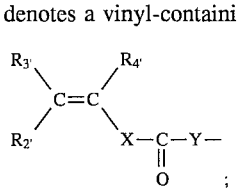

A' denotes an acrylic-containing group having the formula:

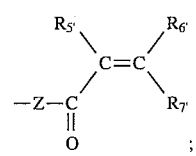

S denotes a styrene-containing group having the formula:

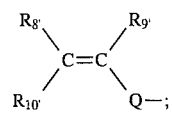

wherein $R_{1'}$ is an alkyl radical derived from substituted and unsubstituted hydrocarbons, polyalkylene oxide, poly(perfluoro) alkylene oxide, dialkyl-capped polydimethylsiloxane, dialkyl-capped polydimethylsiloxane modified with fluoroalkyl or fluoroether groups;

$R_{2'}$–$R_{10'}$ are independently H, or alkyl of 1 to 5 carbon atoms;

Q is an organic group containing aromatic moieties having 6–30 carbon atoms;

X, Y, and Z are independently O, NH or S;

v' is 1, or higher; and a', s' are independently greater than or equal to 0, and a'+ s' is greater than or equal to 1.

These new crosslinking compounds, useful as new polymeric crosslinking agents are suitable for use in the preparation of new hydrogel polymers which, in turn, may be used in the preparation of a wide range of various biomedical devices, such as, contact lenses, surgical devices, heart valves, vessel substitutes, intrauterine devices, membranes and other films, diaphragms, catheters, mouth guards, denture liners, and intraocular devices. The resulting new hydrogels are especially well-suited for the production of contact lenses.

DETAILED DESCRIPTION OF THE INVENTION

Figure 1:
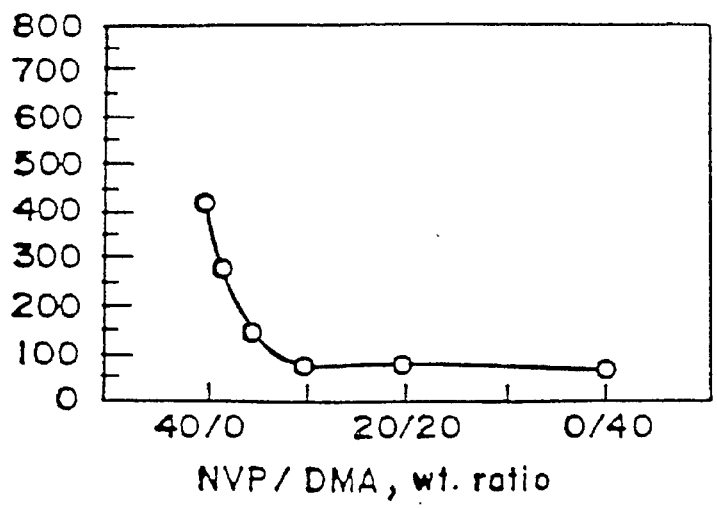
FIGS. 1 and 2 depict the effect on modulus of polyurethane films as the composition ratio of NVP to DMA is changed.

The present invention is directed to new crosslinking agents which link monomers and prepolymers to form new copolymers which are particularly useful as biomedical materials, and are especially useful in contact lens applications. These new crosslinking agents can be used with a wide variety of monomers and prepolymers and can produce a wide variety of contact lens materials such as, for example, hard gas permeable lens materials; soft hydrogel lens materials, soft non-hydrogel lens materials, silicone-containing polymeric materials and non-silicone-containing polymeric materials.

The novel crosslinkers of the present invention can be prepared by employing known organic reaction syntheses to combine the acrylic or styrene group from acrylic-containing or styrene-containing monomers respectively with the vinyl group from the vinyl-containing monomers, such as the preferred vinyl carbonates or vinyl carbamates.

The crosslinkers can be prepared by means of a condensation reaction of an alcohol or an amine which contains an acrylic or styrene group, with, for example vinyl chloroformate under mild reaction conditions (e.g. at ambient temperature or below). The crosslinkers can also be prepared by an addition reaction of the same type of alcohol or amine mentioned above, with vinyl isocyanate at lower temperatures (at or below 10 degrees C.). Both types of reactions are further depicted by the following reaction schemes:

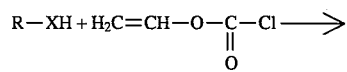 (Condensation Rx)

-continued

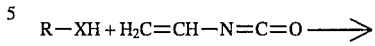

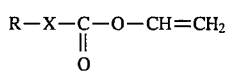

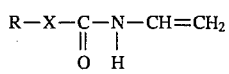

wherein

R is a residue containing an acrylic or a styrene-containing group, or both; and X is NH, O or S.

One preferred example for such a condensation reaction is the reaction of 2-hydroxyethyl methacrylate (HEMA) with vinyl chloroformate to yield methacryloxyethyl vinyl carbonate (HEMAVc). One preferred example of an addition reaction used to produce a novel crosslinker is the reaction of HEMA with vinyl isocyanate to form methacryloxyethyl vinyl carbamate.

A crosslinker having a styrene and vinyl group such as 4-vinylphenyl vinyl carbonate can be produced by reacting 4-vinyl phenol (CTC Organics, Atlanta Ga. and Polysciences, Philadelphia, Pa.), with vinyl chloroformate under mild condensation reaction conditions. Another preferred crosslinker, 4-vinylphenyl carbamate can be prepared in an addition reaction by reacting 4-vinyl phenol with vinyl isocyanate. Alternately, a crosslinker containing a styrene and vinyl group can be prepared by reacting p-chloromethylstyrene (Dow Chemical) with a vinyl carbamate-containing acid under mild reaction conditions, and using 1,8-diazabicyclo[5,4,0]-7-undecene as an acid receptor.

Crosslinkers containing a urea group can be prepared by reacting an ammonium salt containing a styrene or methacrylate moiety, such as 2-aminoethyl methacrylate hydrochloride (Kodak) with vinyl isocyanate under basic conditions at ambient temperature or below.

Vinyl isocyanate, the intermediate useful for making vinyl urea and vinyl carbamate, can be prepared by reacting acrylyl chloride with sodium azide at 10 degrees C. or below, followed by distillation of the product into a cold trap containing an inhibitor such as hydroquinone. (See G. B. Butler and S. B. Monroe, J. Macro. Sci., A5(6), 1063–1070 (1971)).

While the present invention can be used with many polymeric materials including hydrogels, especially preferred are hydrogels, the specific polymers of which may be derived from monomers which may include acrylate, acrylamide, methacrylate, methacrylamide, styrene-containing monomers, dimethacrylate and dimethacrylamide monomers, vinyl amide-containing monomers, vinyl carbonate/carbamate/urea monomers, and (meth)acrylate/(meth)acrylamide-capped prepolymers. All of the above-mentioned monomers and prepolymers may further include polysiloxanes, polyfluorosiloxanes, polyfluoroethers, polyurethanes, and other groups.

One preferred class of suitable silicone-containing monomers contemplated by the present invention are bulky polysiloxanylalkyl (meth)acrylic monomers represented by the formula (II):

$$H_2C=\overset{R}{\underset{|}{C}}-\overset{\phantom{|}}{\underset{\underset{O}{\|}}{C}}-X-(CH_2)_f-\overset{\overset{R^1-\overset{R^1}{\underset{|}{Si}}-R^1}{|}}{\underset{\underset{R^1-\overset{|}{\underset{|}{Si}}-R^1}{\underset{|}{R^1}}}{\underset{|}{Si}}-O-\overset{R^1}{\underset{R^1}{\underset{|}{Si}}}-R^1}} \qquad (II)$$

wherein:

X is O or NR;

each R is independently hydrogen or methyl; and each $R^1$ is independently a lower alkyl or phenyl group; and f is 1 or 3 to 10.

Examples of such bulky monomers include methacryloxypropyl tris(trimethylsiloxy)silane, pentamethyldisiloxanylmethylmethacrylate, tris(trimethylsiloxy)methacryloxy propylsilane, phenyltetramethyldisiloxanylethyl acrylate, and methyldi(trimethylsiloxy)methacryloxymethyl silane.

A further preferred class of silicone-containing prepolymers is a poly(organosiloxane) prepolymer represented by the formula (III):

$$A-(R^7)-\underset{\underset{R^4}{|}}{\overset{\overset{R^3}{|}}{Si}}-[O-\underset{\underset{R^6}{|}}{\overset{\overset{R^5}{|}}{Si}}]_n-O-\underset{\underset{R^4}{|}}{\overset{\overset{R^3}{|}}{Si}}-(R^7)-A \qquad (III)$$

wherein:

A is an activated unsaturated group, such as an ester or amide of an acrylic or a methacrylic acid;

each $R^3$–$R^6$ is independently selected from the group consisting of a monovalent hydrocarbon radical or a halogen substituted monovalent hydrocarbon radical having 1 to 18 carbon atoms which may have ether linkages between carbon atoms;

$R^7$ is a divalent hydrocarbon radical having from 1 to 22 carbon atoms; and n is 0 or an integer greater than or equal to 1.

Another preferred class of silicone containing monomers includes silicone-containing vinyl carbonate or vinyl carbamate monomers of formula (IV):

$$\left[ CH_2=\overset{\overset{R^8}{|}}{C}-(CH_2)_q-O-\overset{\overset{O}{\|}}{C}-Y' \right]_d R^{Si} \qquad (IV)$$

wherein:

Y' denotes —O—, —S— or —NH—;

$R^{Si}$ denotes a silicone-containing organic radical;

$R^8$ denotes hydrogen or methyl;

d is 1, 2, 3 or 4; and q is 0 or 1.

Suitable silicone-containing organic radicals $R^{Si}$ include radicals having any of the following formula:

$$-(CH_2)_n\cdot Si[(CH_2)_m\cdot CH_3]_3;$$

$$-(CH_2)_n\cdot Si[OSi(CH_2)_m\cdot CH_3]_3;$$

$$-(CH_2)_{n'}-\left[\underset{\underset{R^{11}}{|}}{\overset{\overset{R^{11}}{|}}{SiO}}\right]_e-R^{10}; \text{ and}$$

$$-(CH_2)_{n'}-\left[\underset{\underset{R^{11}}{|}}{\overset{\overset{R^{11}}{|}}{SiO}}\right]_e-\underset{\underset{R^{11}}{|}}{\overset{\overset{R^{11}}{|}}{Si}}-R^{c1}$$

wherein:

$R^{10}$ denotes $$-(CH_2)_{p'}-O-\overset{\overset{O}{\|}}{C}-CH=CH_2$$

wherein p' is 1 to 6;

$R^{11}$ denotes an alkyl radical or a fluoroalkyl radical with 1 to 6 carbon atoms;

e is 1 to 200;

n' is 1, 2, 3 or 4; and m' is 0, 1, 2, 3, 4 or 5.

The silicone-containing vinyl carbonate or vinyl carbamate monomers specifically include: 1,3-bis[4-vinyloxycarbonyloxy)but-1-yl]tetramethyl-disiloxane; 3-(trimethylsilyl)propyl vinyl carbonate; 3-(vinyloxycarbonylthio)propyl-[tris(trimethylsiloxy)silane]; 3-[tris(trimethylsiloxy)silyl] propyl vinyl carbamate; 3-[tris(trimethylsiloxy)silyl] propyl allyl carbamate; 3-[tris(trimethylsiloxy)silyl]propyl vinyl carbonate; t-butyldimethylsiloxyethyl vinyl carbonate; trimethylsilylethyl vinyl carbonate; trimethylsilylmethyl vinyl carbonate; and "$V_2D_{25}$", represented by the following formula (V):

$$CH_2=CH-OCO-(CH2)_4-\underset{\underset{CH_3}{|}}{\overset{\overset{CH_3}{|}}{Si}}-O-\left[\underset{\underset{CH_3}{|}}{\overset{\overset{CH_3}{|}}{Si}}-O\right]_{25}-\underset{\underset{CH_3}{|}}{\overset{\overset{CH_3}{|}}{Si}}-(CH2)_4-\overset{\overset{O}{\|}}{OCO}-CH=CH_2 \qquad V.$$

A further preferred class of silicone-containing prepolymers are those monomers having the following schematic representations:

(VI) E(*D*A"*D*G)$_a$*D*A"*D*E'; or (VII) E(*D*G*D*A"$_a$*D*G*D*E';

wherein

D denotes an alkyl diradical, an alkyl cycloalkyl diradical, a cycloalkyl diradical, an aryl diradical or an alkylaryl diradical having 6 to 30 carbon atoms;

G denotes an alkyl diradical, a cycloalkyl diradical, an alkyl cycloalkyl diradical, an aryl diradical or an alkylaryl diradical having 1 to 40 carbon atoms and which may contain ether, thio or amine linkages in the main chain;

* denotes a urethane or ureido linkage;

a is at least 1;

A" denotes a divalent polymeric radical of formula (VIII):

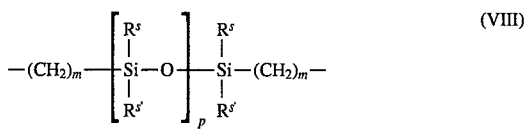

wherein: $R^s$ and $R^{s'}$ independently denote an alkyl or fluoro-substituted alkyl group having 1 to 10 carbon atoms which may contain ether linkages between carbon atoms;

m is at least 1; and p provides a moiety weight of 400 to 10,000;

E and E' independently denote a polymerizable unsaturated organic radical represented by formula (IX):

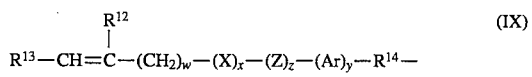

wherein: $R^{14}$ denotes a divalent alkylene radical having 1 to 10 carbon atoms;

$R^{12}$ denotes H or $CH_3$;

$R^{13}$ denotes H, a ($C_1$–$C_6$) alkyl radical or a —CO—Y—$R^{15}$ group wherein Y is —O—, —S— or —NH— and $R^{15}$ is a alkyl radical having 1 to 12 carbon atoms;

X is —CO— or —OCO—;

Z is —O— or —NH—;

Ar denotes an aromatic radical having 6 to 30 carbon atoms;

w is 0 to 6;

x is 0 or 1;

y is 0 or 1; and z is 0 or 1.

Most preferred are the silicone-containing hydrogel contact lenses made from polyurethane hydrogel compositions comprising a urethane prepolymer, a polysiloxanylalkyl methacrylate, at least one acrylic-containing monomer, a vinyl-containing monomer, and the crosslinker of the present invention. The urethane prepolymer is a methacrylate-based prepolymer of the general formula (X):

$R^{16}$ is a diradical of a diisocyanate after removal of the isocyanate group, and is most preferably the diradical of isophorone diisocyanate, and m, p and a are the same as previously defined. Preferably, the sum of m and a is 3 or 4, and more preferably, a is 1 and m is 3 or 4. Preferably, p is at least 30.

Monomer systems for hydrogel lenses often employ a hydrophilic monoolefinic monomer (i.e., a monoethylenically unsaturated monomer) and a polyolefinic (usually diolefinic) monomer (e.g., a polyethylenically unsaturated compound which functions as a crosslinking agent) in an amount sufficient to insolubilize the resulting hydrophilic hydrogel but insufficient to completely mask the hydrophobic properties of the hydrogel. Mixtures of hydrophilic monoolefinic monomers are also used to adjust various properties of the polymeric material, as is well known in the art.

Illustrative hydrophilic monomers include, for example, water soluble monoesters of (meth)acrylic acid with an alcohol having an esterifiable hydroxyl group and at least one additional hydroxyl group such as the mono- and poly-alkylene glycol monoesters of (meth)acrylic acid, e.g., ethylene glycol mono(meth)acrylate, diethylene glycol mono(meth)acrylate, propylene glycol mono(meth)acrylate, dipropylene glycol mono(meth)acrylate, and the like; the N-alkyl and N,N-dialkyl substituted (meth)acrylamides such as N-methyl (meth)acrylamide, N,N-dimethyl (meth)acrylamide, and the like; N-vinylpyrrolidone and the alkyl substituted N-vinyl pyrrolidones; N-vinyl-N-alkyl amides such as N-vinyl-N-methyl acetamide, N-vinyl-N-methylformide, N-vinyl acetamide, N-vinyl formamide; glycidyl (meth)acrylates; the unsaturated amines; the alkoxy ethyl acrylates; fumarates, mixtures thereof; and others known to the art.

Contemplated preferred acrylic-containing monomers identified in Formula I as "Aa"', and which in part comprise the novel crosslinking composition of the present invention, include the (meth)acrylates, (meth)acrylamides, alkyl-(meth)acrylates, alkyl(meth)acrylamides, polysiloxyalkyl-(meth)acrylates, polysiloxyalkyl(meth)acrylamides, fluoroalkyl(meth)acrylates, fluoroalkyl(meth)acrylamides, with the more preferred monomers being 2-hydroxyethyl-

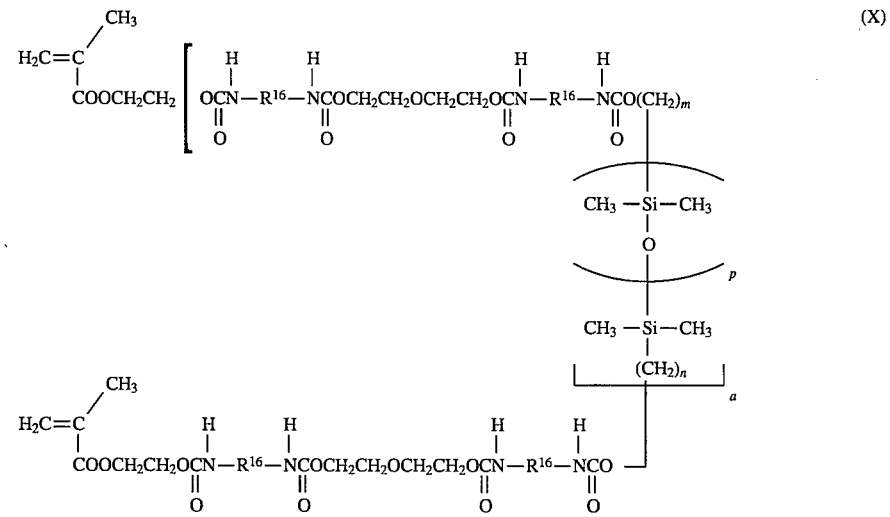

wherein:

methacrylate, glycerol methacrylate, hydroxyethyl methacrylamide, 2-methacrylamido ethanol, N,N-dimethyl acrylamide, N,N-dimethyl methylacrylamide, (meth)acrylic acid and derivatives thereof. The acrylic-containing monomers may further be a prepolymer end-capped with (meth)acrylate- or (meth)acrylamide-containing monomers, with the preferred prepolymers being polysiloxane-, polyalkylene ether-, or polyfluorinated ether-containing monomers and derivatives thereof, all of which may be linked through ester, carbonate, carbamate, urea or urethane linkages. The polysiloxane units in polysiloxane-containing prepolymers may further contain fluoroalkyl, fluoroether, alkyl ether or alcohol groups and derivatives thereof.

The contemplated preferred vinyl-containing monomers present in the novel crosslinker and identified in Formula I as "$V_v$", may include, vinyl carbonate, alkyl vinyl carbonate, polysiloxane vinyl carbonate, fluoroalkyl vinyl carbonate, polysiloxanylalkyl-vinyl carbonate, fluoroalkyl vinyl carbonate monomers, and the corresponding carbamate and urea monomers such as vinyl urea, alkyl vinyl urea, polysiloxanylalkyl vinyl urea and fluoroalkyl vinyl urea monomers. The more preferred vinyl-containing monomers include N-vinylpyrrolidone, N-vinyl,N-methyl acetamide, N-vinyl,N-methyl formamide, N-vinyl acetamide, N-vinyl formamide, and 2-vinyl-4,4 -dimethyl-2-oxazoline-5-one (VDMO) and derivatives thereof.

In addition, the vinyl-containing monomer may be a prepolymer selected from vinyl carbonate-, vinyl carbamate-, and vinyl urea-capped prepolymers and may further comprise polysiloxanes, fluoroalkyl- or fluoroether-containing monomers, and more preferably may include a polyalkylene ether or polyfluorinated ether all of which may be linked through ester, carbonate, carbamate, urea or urethane linkages. The preferred polysiloxane-containing vinyl prepolymers may include an alkyl ether or an alcohol.

The contemplated preferred styrene-containing monomers present in the novel crosslinker and identified in Formula I as "$S_s$", may include 4-vinylphenyl vinyl carbonate, 4-vinylphenylvinyl carbamate, or 4 -vinylphenylvinyl urea and derivatives thereof. Further, the crosslinking agent may comprise all three of an acrylic-, a styrene-, and a vinyl-containing group.

The most preferred crosslinking agents are methacryloxyethyl vinyl carbonate, methacryloxyethyl vinyl carbamate, and methacryloxyethyl vinyl urea.

Preferred novel hydrogel compositions incorporating the novel crosslinker include crosslinkers of the present invention, combined with at least one methacrylate-containing polyurethane-siloxane-containing monomer, and at least one (meth)acrylate or (meth)acrylamide-containing monomer and N-vinyl pyrrolidone. The polyurethane-siloxane-containing monomers may further comprise fluoroalkyl, fluoroether or alcohol-containing monomers. The preferred (meth)acrylates are alkyl methacrylate, 2-hydroxyethyl methacrylate, glycol methacrylate, polysiloxanylalkyl methacrylate and fluoroalkyl methacrylate. The preferred (meth)acrylamide is N,N-dimethyl acrylamide.

The most preferred bulky polysiloxanyl methacrylate is methacryloxypropyl tris(trimethylsiloxy)silane, (TRIS). One preferred hydrogel composition further includes 2-vinyl-4,4-dimethyl-2-oxazolin-5-one (VDMO).

Yet another preferred novel hydrogel composition enabled by the novel crosslinker of the present invention comprises at least one (meth)acrylate- or (meth)acrylamide-capped polysiloxane-containing monomer, a vinyl-containing monomer which may preferably be comprised of carbonate, carbamate and urea-containing polysiloxanyalkylvinyl monomers, or a carboxylic acid-containing vinyl carbonate, vinyl carbamate or vinyl urea, and the crosslinking composition.

Two preferred classes of silicone-containing monomers contemplated by the present invention are urethane-containing prepolymers, and ethylenically terminated polysiloxane containing monomers, such as, most preferably α,ωbis-(methacryloxybutyl)polysiloxane ($M_2D_{25}$).

Another preferred hydrogel comprising the novel crosslinker composition further includes at least a (meth)acrylate-capped fluoroether-modified polysiloxane, a (meth)acrylate- or (meth)acrylamide-containing monomer and N-vinyl pyrrolidone (NVP).

Further, it is envisioned that the new crosslinkers of this invention will react with all known monomers useful in the field of contact lenses, such as, for example HEMA systems, fluoroalkyl containing compositions, silicone- and non-silicone-containing compositions, urethane-containing compositions and silcone-containing compositions.

The polymers of this invention can be formed into contact lenses by spincasting processes (such as those disclosed in U.S. Pat. Nos. 3,408,429 and 3,496,254), cast molding processes (U.S. Pat. Nos. 4,084,459 and 4,197,266), combinations of methods thereof, or any other known method for making contact lenses. Polymerization may be conducted either in a spinning mold, or a stationary mold corresponding to a desired contact lens shape. The lens may be further subjected to mechanical finishing, as occasion demands. Polymerization may also be conducted in an appropriate mold or vessel to form buttons, plates or rods, which may then be processed (e.g., cut or polished via lathe or laser) to give a contact lens having a desired shape.

The hydrogels of the present invention are oxygen transporting, hydrolytically stable, biologically inert, and transparent. The monomers and prepolymers employed in accordance with this invention, are readily polymerized to form three dimensional networks which permit the transport of oxygen and are optically clear, strong and hydrophilic.

The relative softness or hardness of the contact lenses fabricated from the resulting polymer of this invention can be varied by deceasing or increasing the molecular weight of the polysiloxane prepolymer end-capped with the activated unsaturated group or by varying the percent of the comonomer. Generally, as the ratio of polysiloxane units to end-cap units increases, the softness of the material increases.

Any known silicone-containing prepolymer may be used in the process of this invention to form the silicone hydrogels of this invention, as will be apparent to one skilled in the art. The monomers added to the monomer mix to create the monomeric mixture may be monomers or prepolymers.

A "prepolymer" is a reaction intermediate polymer of medium molecular weight having polymerizable groups. Thus it is understood that the terms "silicone-containing monomers" and "hydrophilic monomers" include prepolymers. Examples of such monomers may be found in U.S. Pat. Nos. 4,136,250; 4,153,641; 4,740,533; 5,034,461; and 5,070,215.

As with most random polymeric syntheses, the precise mechanism for the reaction of the new crosslinker with the desired acrylic-, vinyl-, and when desired, styrene-containing monomeric units is not completely understood. However, the resulting end-product polymer systems exhibit superior UV curing capabilities as compared with all known hydrogels to date. Therefore, the invention of this application contemplates all resulting polymeric systems made through reaction of desired monomers with the novel crosslinker, as well as the processes involved in achieving said end-result polymers.

The appropriate amount of the crosslinker used is only dependent upon the desired properties of the resulting hydrogel, such as rigidity. Generally, the concentration of the crosslinker does not exceed 20% by weight of the total monomeric mix, preferably ranges from about 0.001% to about 10%, most preferably ranges from about 0.01% to about 5%, and in each instance should be enough to impart desired properties upon the resulting hydrogel. Typically, an amount of crosslinking agent is added which enables the resulting polymeric hydrogel to absorb water in the range from about 5% to about 90% by weight, preferably from about 10% to about 80%, and most preferably from about 20% to about 75%.

Preferred contact lenses comprising the novel crosslinking composition of the present invention are oxygen permeable, hydrolytically stable, biologically inert, transparent, and can be "hard" or "soft" within the limits of these terms as is understood in the field.

One preferred non-silicone-containing contact lens composition comprises at least one methacrylate such as 2-hydroxymethacrylate or a methyl methacrylate, a vinyl-containing monomer such as N-vinyl pyrrolidone and the crosslinking agent of the present invention.

Polymerization of the monomer mixtures comprising the crosslinker of this invention may be performed in the presence of a diluent. The polymerization product will then be in the form of a gel. If the diluent is nonaqueous, the diluent must be removed from the gel and replaced with water through the use of extraction and hydration protocols well known to those skilled in the art.

It is also possible to perform the polymerization in the absence of diluent to produce a xerogel. These xerogels may then be hydrated to form the hydrogels as is well known in the art.

Notations such as "(meth)acrylate" or "(meth)acrylamide" are used herein to denote optional methyl substitution. Thus, the term methyl (meth)acrylate includes both methyl acrylate and methyl methacrylate. Similarly, the term N-alkyl (meth)acrylamide includes both N-alkyl acrylamide and N-alkyl methacrylamide.

The terms "shaped article for use in biomedical applications" or "biomedical devices" mean the materials disclosed herein have physicochemical properties rendering them suitable for prolonged contact with living tissue, blood and the mucous membranes. These properties are required for biomedical shaped articles as already disclosed. It is known that blood, for example, is readily and rapidly damaged when it comes into contact with artificial surfaces. The design of a synthetic surface which is antithrombogenic and non-hemolytic to blood is necessary for prostheses and devices used with blood.

Therefore, the polymers made from copolymerization with the crosslinkers of the present invention can be used to modify collagen to make blood vessels, urinary bladders surgical diagnostic devices and other such devices as disclosed in Kliment, U.S. Pat. No. 3,563,935. Also polymers can be used to make catheters as disclosed in Shephard U.S. Pat. No. 3,566,874. These polymers can be used as semipermeable sheets for dialysis, artificial dentures and all of such disclosures as set forth in Stoy, U.S. Pat. No. 3,607,848.

Further, the polymers and copolymers disclosed herein can be boiled and/or autoclaved in water without being damaged whereby sterilization may be achieved. Thus, an article formed from the disclosed polymers and copolymers may be used in surgery where an article compatible with living tissue or with the mucous membranes may be used.

The following examples serve only to further illustrate aspects of the invention and should not be construed as limiting the invention. All parts and percents referred to herein are on a weight basis and all viscosities measured at 25 degrees C., unless otherwise specified.

EXAMPLE 1

Preparation of Crosslinker (HEMAVc) Derived From Reaction of Hydroxyethyl Methacrylate and Vinylchloroformate A 500 ml round bottom flask equipped with reflux condenser, mechanical stirrer, thermometer, a dropping funnel and an efficient $N_2$ blanket, was charged with 32.5 g of 2-hydroxyethyl methacrylate, 21.8 g of pyridine and 300 ml of chloroform. The contents were then cooled to less than 5 degrees C. with 25.3 g of vinyl chloroformate added via the dropping funnel while the contents were kept stirred and the temperature maintained below 5 degrees C. The temperature was allowed to rise to ambient temperature and kept stirred overnight. The reaction mixture was then passed through a silica gel column and the contents was then dried with magnesium sulfate and filtered. The solvent was removed under reduced pressure (b.p. 74° C. at 1 mm torr) to give 26 g of named product. GC 99.2% purity. NMR spectrum confirmed the expected structure of the named product.

EXAMPLE 2

Preparation of 4-Vinylphenyl Vinyl Carbonate

A 500 ml round bottom flask equipped with a reflux condenser, a mechanical stirrer, a thermometer, a dropping funnel and an efficient $N_2$ blanket, is charged with 30.0 g (0.25 mole) of 4-vinylphenol, 21.8 g of pyridine and 300 ml of chloroform. The contents are then cooled down to 5 degrees C., and 25,3 g of vinyl chloroformate is added dropwise via the dropping funnel with constant stirring and the temperature maintained at 5 degrees or below. The temperature is then allowed to rise to ambient temperature and the mixture stirred overnight. The reaction mixture is then passed through a silica gel column and dried over magnesium sulfate and filtered. After the solvent is removed under pressure, the named product is recovered.

EXAMPLE 3

Preparation of Methacryloxyethyl Vinyl Carbamate

A 500 ml round bottom flask equipped with a reflux condenser, a mechanical stirrer, a thermometer, a dropping funnel and an efficient $N_2$ blanket, is charged with 32.5 g (0.25 mole) of HEMA, 21.8 g of pyridine, 50 mg of hydroquinone and 300 ml of chloroform. The contents are cooled down to 5 degrees or below. Vinyl isocyanate (13.3 g or 0.25 mole) in chloroform (30 ml) is added dropwise while the reaction contents were stirred and maintained below 5 degrees C. The reaction mixture is stirred for an additional 5 hours. The contents are then passed through a silica gel column, dried over magnesium sulfate and condensed. The residue is distilled under reduced pressure to recover the named product.

EXAMPLE 4

Preparation of 4-Vinylphenyl Vinyl Carbamate

The named is prepared by following the procedure as described in Example 3, except 2-hydroxyethyl methacrylate is replaced by 4-vinylphenol (30 g or 0.35 mole).

EXAMPLE 5

Preparation of Methacryloxyethyl Vinyl Carbamate

A 1 liter round bottom flask equipped with a reflux condenser, a mechanical stirrer, a thermometer, a dropping funnel and an efficient N$_2$ blanket, is charged with 30.5 g (0.5 mole) 2-aminoethanol, 100 mg of hydroquinone, 43.6 g of pyridine and 600 ml of chloroform. The contents are cooled down to between 0 and 5 degrees C. Through the dropping funnel, 50.6 g (0.5 mole) of vinyl chloroformate in 100 ml of chloroform is added into the reaction flask at a rate such that the temperature is maintained at between 0 and 5 degrees C. The temperature is allowed to rise to room temperature with constant stirring overnight. The contents are then passed through a silica gel column, dried with magnesium sulfate and then evaporated. The residue is distilled under reduced pressure to recover 2-hydroxyethyl vinyl carbamate. Then using the same equipment, 32.75 g of 2-hydroxyethyl vinyl carbamate (0.25 mole), 50 mg of hydroquinone, 21.8 g of pyridine, and 300 ml of chloroform are added into the reaction flask and cooled to between 0 and 5 degrees C. Through a dropping funnel, 26.5 g (0.25 mole) of methacryloyl chloride in 50 ml of chloroform is added into the reaction flask at a rate such that the temperature is maintained between 0 and 5 degrees C. The temperature is then allowed to rise to room temperature and the contents stirred overnight. The contents are then passed through a silica gel column, dried with magnesium sulfate and evaporated. The final product is recovered by distillation under reduced pressure.

EXAMPLE 6

Preparation of Methacryloyl Vinyl Urea

A 500 ml 3-necked round bottom flask equipped with a reflux condenser, a mechanical stirrer, a thermometer, a dropping funnel and an efficient N$_2$ blanket, is charged with 2-aminoethyl methacrylate hydrochloride 41.4 g (0.25 mole), 50 mg of hydroquinone and 300 ml of chloroform. The contents are cooled to between 0 and 5 degrees C. and stirred. Through a dropping funnel 25.3 g (0.25 mole) of triethylamine and 13.3 g (0.25 mole) of vinyl isocyanate in 50 ml of chloroform are added into the reaction flask and maintained at between 0 and 5 degrees C. The temperature is allowed to rise to room temperature with the contents stirred constantly overnight, passed through a silica gel column and dried with magnesium sulfate. The contents are then evaporated under reduced pressure to give the named product.

EXAMPLE 7

Preparation of 2-Methacrylamidoethyl Vinyl Carbonate

The named product is prepared by following the same procedure as that described in Example 1, except that 32.2 g (0.25 mole) of 2-hydroxyethyl methacrylamide is used in place of the 2-hydroxyethyl methacrylate.

EXAMPLE 8

Preparation of 2-Methacrylamidoethyl Vinyl Carbamate

The named product is prepared by following the same procedure as described in Example 3, except that 32.2 g (0.25 mole) of 2-hydroxyethyl methacrylamide is used in place of the 2-hydroxyethyl methacrylate.

EXAMPLE 9

Preparation of 2-Methacrylthioethyl Vinyl Carbamate

A 500 ml round bottom, 3-neck flask equipped with a reflux condenser, a mechanical stirrer, a thermometer, a dropping funnel under an N$_2$ blanket, is charged with 2-aminoethyl thiol hydrochloride (Aldrich, 28.4 g or 0.25 mole), hydroquinone (50 mg), pyridine (21.8 g) and chloroform (300 ml). The contents are cooled to 0–5 degrees C. Through the dropping funnel, methacryloyl chloride (26.5 g or 0.25 mole) in 50 ml of chloroform is added at a rate such that the temperature is maintained at between 0 and 5 degrees C. The contents are then stirred overnight and passed through a silica gel column. The mixture is then charged into a new clear similarly equipped round bottom flask along with 50 mg of hydroquinone. The contents are cooled to between 0 and 5 degrees C. Through a dropping funnel, vinyl chloroformate, 25.3 g (0.25 mole), triethylamine (0.25 mole) and 50 ml of chloroform are added into the flask at a rate such that the temperature is maintained between 0 and 5 degrees C. The contents are then allowed to warm to room temperature and kept stirred overnight. The reaction mixture is passed through a silica gel column, dried with magnesium sulfate and condensed. The final product is recovered by distilling the residue under reduced pressure.

EXAMPLE 10

Preparation of Decaethylene Glycol Methacrylate Vinyl Carbonate

The named crosslinker is prepared by following the procedure as described in Example 1, except that 131.5 g (0.25 mole) of decaethylene glycol monomethacrylate (polysciences, Inc.) in the same stoichiometric amount is used to replace 2-hydroxyethyl methacrylate.

EXAMPLE 11

Preparation of Decaethylene Glycol Methacrylate Vinyl Carbamate

The named crosslinker is prepared by following the same procedure as described in Example 3, except that decaethylene glycol monomethacrylate in the same stoichiometric amount is used to replace 2-hydroxyethyl methacrylate.

EXAMPLE 12

Preparation of 4-Methacrylamidophenyl Vinyl Carbonate

The named compound is prepared by following the same procedure as that described in Example 7 except that 27.3 g (0.25 mole) 4-aminophenol is used to replace 2-amino ethanol in the reaction.

EXAMPLE 13

Preparation of 4-Methacrylamidophenyl Vinyl Carbamate

The named product is prepared by following the procedure set forth in Example 12 except that 13.3 g (0.25 mole) of vinyl isocyanate is used to replace vinyl chloroformate.

EXAMPLE 14

Preparation of 1-(4-Methacryloxybutyl)-3-(4-Vinyloxycarboxybutyl)tetramethyl Disiloxane A 500 ml 3-neck, round bottom flask equipped with a reflux condenser, a mechanocal stirrer, a thermometer, a dropping funnel and a $N_2$ blanket, is charged with 69.5 g (0.25 mole) of 1,3-bis(4-hydroxybutyl) tetramethyl disiloxane (Silar Lab.), pyridine, 19.5 g and 300 ml of methylene chloride. The contents are cooled down to between 0 and 5 degrees C. by an ice bath. Through the dropping funnel 25.3 g (0.25 mole) of vinyl chloroformate in 50 ml of methylene chloride is added dropwise into the flask at a rate such that the temperature is maintained between 0 and 5 degrees C. The contents are then stirred for another 4 hours and then passed through a silica gel column. The eluents are condensed and injected in 6–8 gram portions into a reverse phase high performance liquid chromatography unit (Waters), using acetonitrile as solvent. Three fractions are collected. The major (center) fraction from each injection is collected and condensed to give 1,3-bis(4-hydroxybutyl)tetramethyl disiloxane monovinyl carbonate. The monovinyl carbonate product (34.8 g or 0.1 mole) is charged into a flask as already described, along with 8.0 g of pyridine, 50 mg of hydroquinone and 200 ml of chloroform. The contents are cooled down to between 0 and 5 degrees C. Through a dropping funnel, 10.5 g (0.1 mole) of methacryloyl chloride in 50 ml of chloroform is added into the flask at such a rate that the temperature is maintained between 0 and 5 degrees C. The contents are stirred continuously for 4 hours and then passed through a silica gel column. The contents are then condensed and distilled under reduced pressure to give the named product. Hydroquinone (50 mg) is added into the named product.

EXAMPLE 15

Preparation of -(4-Vinyloxycarboxybutyl)dimethylsilyl-(4-methacryloxybutyl)dimethylsiloxy Polysiloxane A one liter, 3-neck round bottom flask equipped with a reflux condenser and mechanical stirrer, is charged with the 8.08 g (0.02 mole) of the crosslinker prepared according to the method as described in Example 14, and 35.52 g (0.12 mole) octamethylcyclotetrasiloxane.

EXAMPLE 16

Preparation of 2,2,3,3-Tetrafluoro-1,4-butanediol Methacrylate Vinyl Carbonate The named compound is prepared according to the procedure described in Example 14, except that 1,3 -bis(4-hydroxybutyl)tetramethyldisiloxane is replaced by 40.5 g (0.25 mole) of 2,2,3,3,-tetrafluoro-1,4 -butanediol (PCR, Inc.)

EXAMPLES 17–22

Formulations Containing HEMA and NVP (Non-silicone)

The HEMA used in formulations (Examples) 17 and 18 contained 0.06% ethylene glycol dimethacrylate (EGDMA). In both of Examples 17 and 18, two films were cast. Formulations 17A and 18A were subjected to both a thermal heat cure followed by a UV cure. Formulations 17B and 18B were subjected to only UV curing. The HEMA used in formulations (Examples) 19 and 22 contained 0.15% EGDMA. The formulations were subjected to curing conditions comprising either only UV for one hour, or UV followed by a heat postcure at 120 degrees C. for one additional hour. The UV initiator used was benzoin methyl ether (BME) or Darocure-1173 (EM Industries). The thermal initiator used was tertbutyl peroctoate (TBO). The films were cast between two glass plates, followed by boiling water extraction and then placed in a phosphate buffered saline before evaluating physical characteristics.

| Formulation | Examples | | | | | |
|---|---|---|---|---|---|---|
| (parts) | 17 | 18 | 19 | 20 | 21 | 22 |
| HEMA | 72 | 72 | 72 | 72 | 72 | 72 |
| NVP | 28 | 28 | 28 | 28 | 28 | 28 |
| BME | 0.076 | 0.076 | — | — | — | — |
| TBO | 0.100 | 0.100 | — | — | — | — |
| Darocur | — | — | 0.2 | 0.2 | 0.2 | 0.2 |
| REMAVc | — | — | — | — | 0.2 | — |
| EGDMA | — | 20 | — | 20 | 20 | 20 |
| Glycerin | 20 | — | 20 | 20 | 20 | 20 |

| Curing Type | Examples | | | | | | | |
|---|---|---|---|---|---|---|---|---|
| Formulation | 17A | 17B | 18A | 18B | 19 | 20 | 21 | 22 |
| UV | yes | yes | yes | yes | yes | yes | yes | yes |
| Heat | yes | no | yes | no | no | no | no | no |

| Film | Examples | | | | | | | |
|---|---|---|---|---|---|---|---|---|
| Properties | 17A | 17B | 18A | 18B | 19 | 20 | 21 | 22 |
| % Extr | 18 | 78 | 5.2 | 13.1 | 13.0 | 12.8 | 10.7 | 12.2 |
| % Water | 54 | 80 | 56 | 55.3 | 56.2 | 56.7 | 58.4 | 54.0 |
| Modulus | 25 | — | 28.8 | 23.5 | 25.5 | 24.1 | 17.1 | 28.7 |
| Tear | 3.0 | — | 2.6 | 4.4 | 4.4 | 4.7 | 3.2 | 2.1 |

Results

The results show that the formulation using the novel crosslinker, HEMAVc (Example 21) was able to produce films with a lower amount of extractables and increased water content, while being cured with only UV, These results are believed to show better incorporation of HEMA with NVP under only a UV cure regimen when the novel crosslinker, HEMAVc is present. The hydrogel lens made from this formulation (Example 21) gave an optical quality of 4.8 out of a 5.0 scale which was far superior to the only comparative formulation cast into lenses (Example 17) which had a 4.0 optical clarity rating.

EXAMPLES 23–30

To further exemplify the enhanced performance of the novel crosslinker, HEMAVc as compared with traditional crosslinkers, such as EGDMA, the formulations from Examples 21 and 22 were further modified by adding increased concentrations of HEMAVc. All films cast were UV cured for one hour followed by standard extraction procedures as already described. The following properties were noted.

| | Examples | | | | | | | |
|---|---|---|---|---|---|---|---|---|
| | 23 | 24 | 25 | 26 | 27 | 28 | 29 | 30 |
| HEMAVc | 0.2 | 0.4 | 0.8 | 1.6 | 0.2 | 0.4 | 0.8 | 1.6 |

-continued

| | Examples | | | | | | | |
|---|---|---|---|---|---|---|---|---|
| | 23 | 24 | 25 | 26 | 27 | 28 | 29 | 30 |
| Conc. | | | | | | | | |
| Film | | | | | | | | |
| Properties | | | | | | | | |
| % Extract | 10.7 | 7.8 | 7.1 | 5.7 | 12.2 | 8.0 | 7.6 | 6.9 |
| % Water | 58.4 | 57.7 | 55.8 | 53.7 | 54.0 | 54.6 | 53.5 | 50.7 |
| Modulus | 17 | 22 | 38 | 60 | 29 | 42 | 53 | 87 |
| Tear | 3.2 | 3.0 | 2.3 | 2.5 | 2.1 | 1.6 | 1.5 | 1.6 |

EXAMPLE 31–36

Preparation of Non-Silicone-Containing Hydrogels With HEMAVc

To further exemplify the usefulness of the crosslinking agent of the present invention with varied polymeric systems, HEMAVc was used as the crosslinking agent in non-silicone-containing formulations containing both a hydrophilic methacrylate (HEMA) and a hydrophobic methacrylate (4-t-butyl-2-hydroxycyclohexyl methacrylate, or TBE) and NVP. All formulations were cured with UV and the resulting films were optically clear. The properties of the films cast from the various formulations are shown in the following table:

| | Example | | | | | |
|---|---|---|---|---|---|---|
| Formulation | 31 | 32 | 33 | 34 | 35 | 36 |
| HEMA | 55 | 55 | 55 | 50 | 45 | 40 |
| NVP | 45 | 45 | 45 | 50 | 55 | 60 |
| HEMAVc | .3 | .3 | .3 | .3 | .3 | .3 |
| DAROCURE | .2 | .2 | .2 | .2 | .2 | .2 |
| GLYCERIN | 20 | 20 | 20 | 20 | 20 | 20 |
| TBE | 5 | 10 | 15 | 15 | 20 | 20 |
| Properties | | | | | | |
| % Extract | 6.8 | 4.9 | 5.9 | 5.2 | 8.1 | 8.1 |
| % Water | 69 | 63 | 59 | 67 | 64 | 64 |
| Modulus | 13 | 17 | 46 | 18 | 680 | 490 |
| Tear | 2.6 | 4.7 | 12.1 | 6.5 | high | high |

EXAMPLE 37

Preparation Of Polyurethane-silicone Hydrogels

A monomer mix for a polyurethane hydrogel containing the following components was prepared:

a) urethane prepolymer, derived from isophorone diisocyanate, diethylene glycol, polysiloxanediol of molecular weight 3600 and end-capped with HEMA (IDS3H), 30 parts;
b) 3-methacryloxypropyl tris(trimethylsiloxy)silane, (TRIS), 30 parts;
c) NVP, 40 parts;
d) n-hexanol; and
e) Darocur-1173, 0.2 parts.

To a portion of the above-identified formulation was added 0.6 part HEMAVc. Both mixes were then processed into hydrogel films by placing the mix between two glass plates and curing under UV for 2 hours followed by extraction with ethanol for 4 hours followed by boiling water for 4 hours. The hydrogel films were then placed in a phosphate buffered saline (pH 7.4) solution. The following properties were noted.

| | Formulation | |
|---|---|---|
| Properties | without HEMAVc | with HEMAVc |
| % Extract | 16 | 10 |
| % water | 25 | 37 |
| Oxygen Perm, Dk | 144 | 105 |
| Modulus, g/mm$^2$ | 970 | 430 |

The formulation containing the novel crosslinker exhibited improved characteristics such as lower extractables, higher water content and lower modulus without sacrificing much oxygenpermeability.

EXAMPLE 38

A monomer mix was prepared, derived from the following IDS3H/TRIS/NVP/DMA/HEXANOL/DAROCUR-1173 ats the following weight ratios 25/25/35/15/40/0.2. Formulations "A" through "I" were established with "A" being the comparative control containing no crosslinker, "B" through "E" containing progressively increasing amounts of HEMAVc, and "F" through "I" containing progressively increasing amounts of EGDMA. The mixes were then cast into hydrogel films using procedures as earlier described. The film properties for each formulation were noted and are produced in the following table:

| | Formulation | | | | | | | | |
|---|---|---|---|---|---|---|---|---|---|
| | A | B | C | D | E | F | G | H | I |
| | | | | | Crosslinker | | | | |
| | | | HEMAVc | | | | EGDMA | | |
| weight % | 0 | 0.1 | 0.2 | 0.4 | 0.8 | 0.1 | 0.2 | 0.4 | 0.8 |
| % Ext | 15.9 | 12.6 | 11.2 | 8.2 | 6.1 | 16.2 | 14.5 | 14.1 | 13.2 |
| % H$_2$O | 47.4 | 49.3 | 51.4 | 50 | 47.0 | 46.1 | 46.5 | 45.0 | 43.4 |
| Mod. | 56 | 51 | 59 | 67 | 98 | 60 | 66 | 74 | 119 |

Results

In the formulations containing HEMAVc, extractables and modulus values were comparatively lower, and the water content values comparatively higher than the formulations which did not contain HEMAVc.

EXAMPLE 39

Casting Hydrogel Films—HEMA/NVP Formulation Containing HEMAVc

A formulation containing hydroxyethyl methacrylate (HEMA) which in turn contained 0.17% ethyleneglycol dimethacrylate (EGDMA) 72 parts; 1-vinyl-2-pyrrolidone (NVP), 28 parts; hydroxyethyl methacrylate vinylchloroformate, 0.08 parts; Darocur-1173 [EM Industries], 20 parts; and hexanol, 20 parts was prepared. This formulation was cast between two silane-treated glass plates and cured under UV radiation for 2 hours. After solvent (ethanol) extraction, the weight loss was 14.5%, which was accountable for the weight of the hexanol. The films after hydration contained 65% water, indicating excellent polymerization.

EXAMPLE 40

HEMA/NVP Formulation Without HEMAVc

The mix containing HEMA/EGDMA/NVP/Benzoin methylether (BME)/t-butylperoxyoctoate (TBO) (71.85/ 0.15/28/0.75/0.1) was cast into lenses by first exposing to ultraviolet radiation (UV) for 2 hours, followed by 120 degree C. heat postcure for 1 hour. The resulting lenses were then extracted with boiling water. The boiling water extractables was 18% and the final water content of the lens was 56.5%. When comparing the data from HEMAVc modified formulation and the standard formulation, it was believed that more NVP was incorporated into the hydrogel in the HEMAVc modified formulation. Most importantly, the copolymerization or curing for the HEMAVc-modified formulation can be achieved by exposure to UV radiation alone, instead of using a heated post-cure regimen as is required for the standard formulation.

EXAMPLE 41

Urethane Hydrogels for Contact Lens Applications

A monomer mix containing the following ingredients was prepared.

a) 30 parts urethane prepolymer derived from isophorone diisocyanate, diethylene glycol, polysiloxanediol of molecular weight 3600 b) 30 parts of TRIS c) 30 parts of NVP d) 10 parts of DMA e) 0.1 parts of crosslinker HEMAVc f) 0.2 parts of Darocure-1173 g) 40 parts of solvent hexanol

This formulation was cured under UV radiation for 2 hours to form films, which were then extracted with ethanol, dried and boiled in water, followed by saturation in buffered saline at pH 7.4. The hydrogel films had a modulus value of 80 g/mm2, oxygen permeability of 98 in Dk units, and water content of 41%.

EXAMPLE 42

Urethane Hydrogel Formulation Containing NVP, DMA, VDMO and HEMAVc

A monomer mix containing the same ingredients in the same weight ratio as that in Example 41 except that 10 parts of 2-vinyl-4,4-dimethyl-2-oxazoline-5-one (VDMO) was added. The formulations can be processed into the hydrogel films of Example 10. The hydrogel films had a modulus value of 110 g/mm$^2$. Oxygen permeability of 90 (Dk units) and a water content of 40%.

EXAMPLE 43

Urethane Hydrogel Lens Casting

A polyurethane mix of the formulation as described in Examples 41 and 42 was filtered through a disposable filter into a clean vial. Under an inert nitrogen atmosphere, 60–90 microliters of the mix was injected onto a clean plastic mold half and then covered with a second plastic mold half. The molds were then compressed and cured for 90 minutes in the presence of UV light (4200 microwatts/cm$^2$). The molds were then opened mechanically and put into a beaker containing aqueous ethanol. The lenses were released from the molds within 1 hour, then extracted with ethanol for 48 hours, and boiled in distilled water for 4 hours. The resultant lenses were inspected for cosmetic quality, cytotoxicity and dimension. Lenses passing inspection were thermally disinfected in phosphate buffered saline prior to on-eye evaluation.

EXAMPLE 44

Clinical Evaluations

The cast-molded polyurethane lenses described in Example 43 were evaluated on six to 10 patients. In each test, a poly(HEMA) control lens was worn on one eye and the test lens on the other eye. The lenses were analyzed after a minimum of one hour, and preferably 5 hours or longer for wettability and surface deposition study. The surface wettability rating scale was 0–4 with 0 representing no surface deposit and 4 representing multiple deposits of 0.5 mm diameter or larger. The results for the lenses of the formulation of Example 41, was 3.0 for wetting and 0.4 for deposits after 5 hours of wear. For lenses comprising 1 part VDMO (Example 42 formulation), the results showed a wettability rating of 3.3 and a deposit rating of 0.7 after 4 hours of wear.

EXAMPLE 45

Formulation Containing M$_2$D$_{25}$/TRIS/NVP/HEMAVc

An α,ω-Bis(methacryloxybutyl)polysiloxane (M$_2$D$_{25}$) was prepared from the reaction of 1,3-Bis(4-methacryloxybutyl)disiloxane and 1,1,3,3,5,5-hexamethyl trisiloxane in molar ratio of 1:8.33. Thirteen parts of M$_2$D$_{25}$ was combined with 47 parts of TRIS, 40 parts of NVP, and 0.1 part of HEMAVc was shaken and produced a clear solution. To this mixture was added 40 parts of hexanol and 0.2 parts of Darocure-1173. Twenty (20) parts of hexanol was added to the mixture along with 0.2 parts of BME. The resultant formulation was cast onto glass plates and cured under UV light for 2 hours. The films were extracted with solvent (ethanol) overnight, boiled in water for 4 hours, and then placed in buffered saline at pH 7.4. These films exhibited the following properties: water content—23%; modulus 369 g/mm2; contact angle—20 degrees; and oxygen permeability 114 in Dk units.

EXAMPLE 46

Formulation Containing M$_2$D$_{25}$/TRIS/NVP/DMA/HemaVc

A glass vial contained the above-listed ingredients in the following amounts: (13/47/30/10/0.1). The content was cast into hydrogel films according to the procedure described in Example 45. The resultant hydrogel films exhibited the following properties: water content—24%; modulus 146 g/mm2; contact angle 25 degrees; and oxygen permeability 113 in Dk units.

EXAMPLE 47

Comparative Formulation—$M_2D_{25}$/NVP/DMA/HemaVc

A formulation was prepared containing the same weight ratio as that in Example 46 immediately above, except that TRIS was replaced completely by an additional amount of $M_2D_{25}$ (60/30/10/0.1). The resulting mixture was cast into hydrogel films according to the procedure described in Example 39. The resultant films exhibited a modulus of 570 g/mm2 (which is about 1.5 times greater than the modulus displayed by the hydrogel films prepared as described in Example 14 which contained both $M_2D_{25}$ and TRIS in the specified weight ratio of 13 to 47.

EXAMPLES 48–53

Six polyurethane hydrogel films containing the following ingredients, were prepared:
a) urethane prepolymer, derived from isophorone diisocyanate, diethylene glycol, polysiloxanediol of molecular weight 3600 and HEMA, 30 parts;
b) TRIS, 30 parts;
c) NVP, varied from 0 to 40 parts;
d) DMA, varied from 40 to 0 parts (NVP+ DMA= 40 parts)
e) HEMAVc crosslinker at 0.3% of NVP amount;
f) n-Hexanol 40 parts;
g) Darocur-1173, (UV initiator), 0.2 part.

These formulations were UV cured, followed by ethanol extraction and boiling water hydration, to give resultant hydrogel films with the following properties (water content and modulus). FIG. 1 depicts the resultant films of Examples 48–53 as shown in Table 1, with each film as one plotted point respectively.

TABLE 1

|  | Example | | | | | |
|---|---|---|---|---|---|---|
|  | 48 | 49 | 50 | 51 | 52 | 53 |
| NVP/DMA ratio | 40/0 | 38/2 | 35/5 | 30/10 | 20/20 | 0/40 |
| % water | 35 | 46 | 44 | 41 | 41 | 37 |
| Modulus | 430 | 281 | 150 | 80 | 79 | 63 |

Results

FIG. 1 depicts the resultant film of Examples 54–57, with the modulus/composition relationship of each film plotted as one point respectively.

EXAMPLES 54–57

Polyurethane formulations of the ingredients as in Examples 48–53 but of different relative parts, as shown in Table 2, were prepared.
a) IDS3H & b) TRIS, 34 parts each;
c) NVP & d) DMA, 32 parts combined;
e) n-Hexanol, f) HEMAVc and g) Darocure-1173, same parts as in Examples 48–53.

Figure 2:
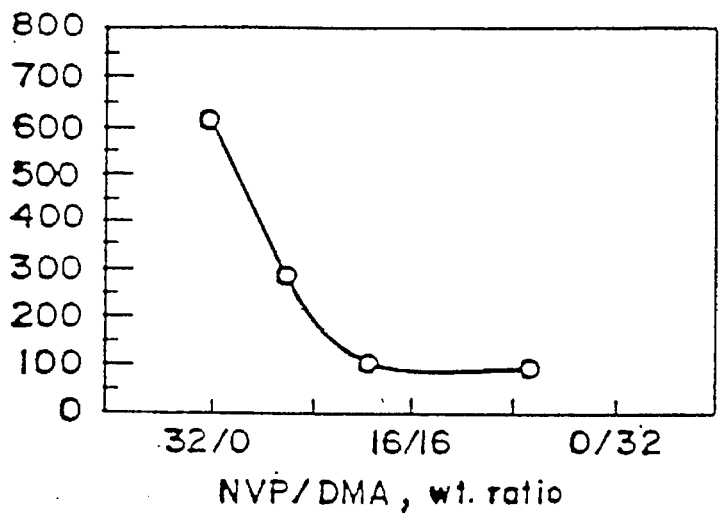

The formulations were cast and processed in the same manner as in Examples 48–53, with the water content and modulus data shown in Table 2. FIG. 2 depicts the resultant film of Examples 54–57, with each film as one plotted point respectively.

TABLE 2

|  | Example | | | |
|---|---|---|---|---|
|  | 54 | 55 | 56 | 57 |
| NVP/DMA ratio | 32/0 | 24/8 | 16/16 | 0/32 |
| water % | 25 | 26 | 31 | 25 |
| Modulus | 610 | 275 | 107 | 87 |

The modulus/composition relationship is further shown in FIG. 2.

EXAMPLES 58–61

$M_2D_x$-based Hydrogel Films

Figure 3:
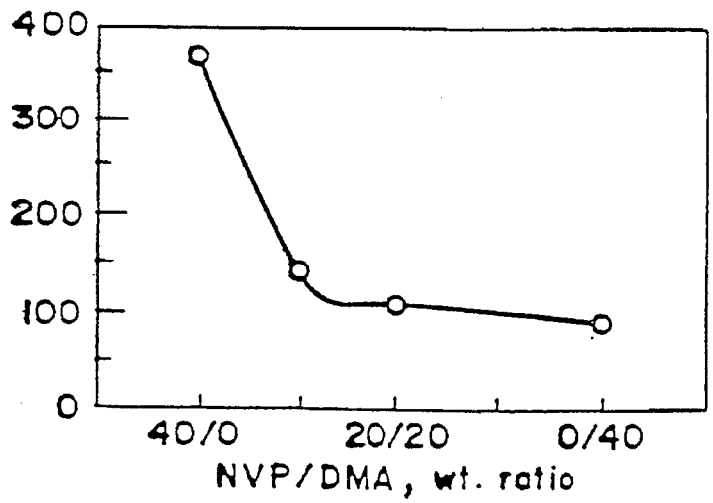
FIG. 3 depicts the effect on modulus of methacrylate-capped polysiloxane films as the composition ratio of NVP to DMA is changed.

The following silicone-containing hydrogel formulations were prepared and cast processed into hydrogel films by the procedure of Examples 48–53. The ingredients were:
a) $M_2D_{25}$, 13 parts
b) TRIS, 47 parts
c) NVP & d) DMA, 40 parts combined
e) n-Hexanol, 40 parts
f) HEMAVc, 0.3 part of NVP amount
g) Darocure, 0.2 part The formulations were cast and processed in the same manner as in Examples 48–53, with the water content and modulus data shown in Table 3. FIG. 3 depicts the resultant film of Examples 58–61, with each film as one plotted point respectively.

TABLE 3

|  | Example | | | |
|---|---|---|---|---|
|  | 58 | 59 | 60 | 61 |
| NVP/DMA ratio | 40/0 | 30/10 | 20/20 | 0/40 |
| water % | 23 | 24 | 32 | 29 |
| Modulus | 370 | 150 | 110 | 90 |

Many other modifications and variations of the present invention are possible to the skilled practitioner in the field in light of the teachings herein. It is therefore understood that, within the scope of the claims, the present invention can be practiced other than as herein specifically described.

I claim:

1. A composition having at least two different types of ethylenically polymerizable groups and having the schematic representation:

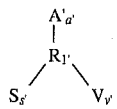

wherein

V denotes a vinyl-containing group having the formula:

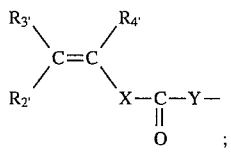

A' denotes an acrylic-containing group having the formula:

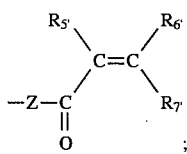

S denotes a styrene-containing group having the formula:

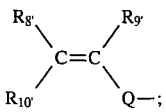

wherein $R_{1'}$ is an alkyl radical, polyalkylene oxide, poly(perfluoro) alkylene oxide, dialkyl-capped polydimethylsiloxane, dialkyl-capped polydimethylsiloxane modified with fluoroalkyl or fluoroether groups;

$R_{2'}$–$R_{10'}$ are independently H, or alkyl of 1 to 5 carbon atoms;

Q is an organic group containing aromatic moieties having 6–30 carbon atoms;

X, Y, and Z are independently O, NH or S;

v' is 1, or higher; and a', s' are independently greater than or equal to 0, and a'+s' is greater than or equal to 1.

2. The composition of claim 1 wherein $R_{1'}$ is an alkyl radical.

3. The composition of claim 2 wherein $R_{1'}$ is an ethyl group.

4. The composition of claim 1 wherein the composition comprises at least one acrylic-containing group and at least one vinyl-containing group.

5. The composition of claim 4 wherein the acrylic-containing group is selected from the group consisting of an alkyl (meth)acrylate, alkyl (meth)acrylamide, fluoroalkyl(meth)acrylate, and fluoroalkyl(meth)acrylamide.

6. The composition of claim 5 wherein the alkyl (meth)acrylate or alkyl (meth)acrylamide group is selected from the group consisting of derivatives of 2-hydroxyethyl methacrylate, glycerol methacrylate, hydroxyethyl methacrylamide, N,N-dimethylacrylamide, and 2-methacrylamido ethanol.

7. The composition of claim 1 wherein at least one polysiloxane-containing group is linked to at least one polyalkylene ether-containing group through ester, carbonate, carbamate, urea or urethane linkages.

8. The composition of claim 4 wherein the vinyl-containing group is selected from the group consisting of vinyl carbonates, vinyl carbamates and vinyl ureas.

9. The composition of claim 8 wherein the vinyl-containing group is a vinyl carbonate.

10. The composition of claim 8 wherein the vinyl-containing group is a vinyl carbamate.

11. The composition of claim 8 wherein the vinyl-containing group is a vinyl urea.

12. The compound methacryloxyethyl vinyl carbonate.

13. The compound methacryloxyethyl vinyl carbamate.

14. The compound methacryloxyethyl vinyl urea.

* * * * *